United States Patent [19]

Davis

[11] Patent Number: 4,766,119

[45] Date of Patent: * Aug. 23, 1988

[54] ANTISPASMODIC ALKYLATED AMINOTHIOESTER DERIVATIVES

[75] Inventor: William M. Davis, Tucson, Ariz.

[73] Assignee: United Pharmaceuticals, Inc., Tucson, Ariz.

[*] Notice: The portion of the term of this patent subsequent to Mar. 3, 2004 has been disclaimed.

[21] Appl. No.: 703,281

[22] Filed: Feb. 20, 1985

[51] Int. Cl.$^4$ .................. A61K 31/40; A61K 31/445; A61K 31/535; A61K 31/265
[52] U.S. Cl. ......................... 514/239.2; 514/315; 514/428; 514/513; 544/158; 546/248; 548/573; 558/256
[58] Field of Search ............... 514/513, 428, 315, 228; 260/455 R; 558/256; 548/573; 546/248; 544/158

[56] References Cited

U.S. PATENT DOCUMENTS

| | | | |
|---|---|---|---|
| 2,390,555 | 12/1945 | Richardson | 260/455 R X |
| 2,510,773 | 6/1950 | Clinton | 546/203 X |
| 3,435,007 | 3/1969 | Starkovsky et al. | 546/5 X |
| 3,671,527 | 6/1972 | Krimmel | 260/455 R X |
| 3,989,686 | 11/1976 | Phillipps et al. | 260/239.55 R |
| 4,432,977 | 2/1984 | Davis | 514/513 |
| 4,647,562 | 3/1987 | Davis | 514/228 X |
| 4,652,649 | 3/1987 | Davis | 558/256 X |

FOREIGN PATENT DOCUMENTS

| | | | |
|---|---|---|---|
| 0125508 | 11/1984 | European Pat. Off. | 514/513 |
| 57-70860 | 5/1982 | Japan | 514/513 |

OTHER PUBLICATIONS

Dupre et al.; Compte Rendu de la Societe de Biologie, 140, (1946), pp. 477-479.
Tchoubar et al.; Bulletin de la Societe Chimique, (1947), pp. 792-794.
Liberman; Farmakol. i. Toksikol., (1956), pp. 10-17.
Chemical Abstracts Service—Registry Handbook-Number Section, 1981 Supplement, p. 2771 RJ.
Neises et al., C. A., 95, 186795c, (1981), vol. 95.

Primary Examiner—Joseph Paul Brust
Attorney, Agent, or Firm—Austin R. Miller

[57] ABSTRACT

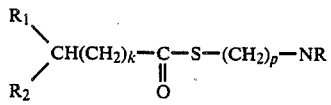

wherein
$R_1$ and $R_2$ are straight chain or branched alkyl groups from one to eight carbon atoms, and are independent alkyl groups not interconnected and k is an integer from zero to five, and the total number of carbon atoms in $R_1$ and $R_2$ plus k are equal to or less than twelve, and wherein
p is an integer from one to three;
NR is selected from the group consisting of pyrrolidino, piperidino, morpholino and dialkylamino containing a total of two to eight carbon atoms either straight chain or branched; or pharmaceutically acceptable salts thereof.

14 Claims, No Drawings

ANTISPASMODIC ALKYLATED AMINOTHIOESTER DERIVATIVES

BACKGROUND OF THE INVENTION

1. Field of the Invention

The present invention relates to new pharmaceutical compounds having useful anti-spasmodic properties.

2. Description of the Prior Art

The purpose of an anti-spasmodic drug is to relieve spasms of the smooth muscles. Smooth muscles line most of the visceral organs. The peristalsis and muscular activity of the stomach, intestines, gall bladder, urinary bladder, lung, the uterus, and to a degree the heart are all largely controlled by smooth muscles. Smooth muscles are innervated by the autonomic nervous system. The autonomic nervous system consists of two antagonistic branches—the sympathetic branch and the parasympathetic branch. On all visceral organs except the heart the parasympathetic nerve impulses increase the irritability and tension of the smooth muscles; contrariwise, the sympathetic nerve impulses increase the tension and irritability of the muscles of the heart muscle and relax the smooth muscles of the other visceral organs.

A spasm in a smooth muscle may be due to one of two causes. Either the smooth muscle may be receiving exaggerated impulses from the autonomic nervous system which create violent contractions in the muscle, or the muscle may be intrinsically stimulated into a spasm (most likely from chemical changes in the surrounding tissue). A spasm due to exaggerated impulses from the parasympathetic branch of the autonomic nervous system may often be corrected by administering atropine (an active alkaloid of belladonna which serves to break a connection between the parasympathetic nerve and the smooth muscle. This ability and effect of atropine is called a "neurotropic effect". A spasm intrinsic in the smooth muscle itself may often be corrected by papaverine (a derivative of opium which is classed as a narcotic). Papaverine has an ability to decrease intrinsically the contractility of smooth muscle; it has the ability to relax smooth muscles directly. This ability and effect of papaverine is called a "musculotropic effect."

In relieving spasms of smooth muscles generally, a musculotropic effect is acknowledged to be superior to a neurotropic effect. A neurotropic effect cannot relieve spasms intrinsic in the smooth muscle itself, while a musculotropic effect, by relaxing and decreasing the irritability and responsiveness of smooth muscle to stimulation from the autonomic nervous system, can help to relieve a smooth muscle spasm even when it is due to exaggerated impulses from the autonomic nervous system.

A clinical difficulty with atropine is that of undesirable side-reactions. Atropine when given in effective doses, serves to break or partly break all the parasympathetic nerve-smooth muscle connections throughout the body. Thus when atropine is given in sufficient dosage to relieve a spasm in a specific visceral organ, such as a gastric or intestinal spasm (the spasm caused by exaggerated nerve impulses from the parasympathetic nervous system) undesirable side-actions due to the breaking of the parasympathetic nerve-muscle connections elsewhere in the body may occur. The most easily recognized of these undesirable side reactions are dilation of the pupil and dryness of the mouth, caused by the breaking of the parasympathetic connections to the iris and the saliva producing mechanism respectively.

Atropine is acknowledged to have also a musculotropic effect, but its neurotropic effect is so strong that it cannot be given in greater than minute doses (1/60 to 1/40 grain) without encountering the undesirable side reactions. This dosage is too small to permit a significant musculotropic effect.

U.S. Pat. No. 2,390,555 discloses a class of compounds comprising di-N-substituted aminoethyl esters of diphenylthioacetic acid of the general formula $(C_6H_5)_2$—CH—COS—$CH_2CH_2$—R in which R represents a disubstituted amino radical of either the diethylamino group, the morpholino group or the piperidino group. This patent was based upon the discovery that the thio analogs of certain disubstituted acetic acid esters of aminoalcohols have desirable anti-spasmodic properties. These compounds have proven to be very effective and are widely used as anti-spasmodics without encountering the undesirable side reactions due to excessive neurotropic effect.

U.S. Pat. No. 4,432,977 discloses new uses, especially for the dilation of the smooth muscles of the upper urinary tract, of the compounds disclosed in U.S. Pat. No. 2,390,555.

In *Compte Rendu de la Societe de Biologie*, 140, pp 477–9, (1946) Dupre, Levy and Tchoubar disclose a series of compounds having the formula $C_6H_5(R)CH$—$C(O)$—S—$CH_2CH_2N(CH_2CH_3)_2$ where R is either a phenyl group, a propyl group, an isopropyl group, a butyl group or an isoamyl group. These compounds are all disclosed as being spasmolitic agents.

Compounds of the same general formula given above were prepared by Tchoubar and Letellier-Dupre in *Bulletin de la Societe Chimique*, pp 792–4 (1947) wherein R was a phenyl group, an ethyl group, a propyl group, an isopropyl group, a butyl group, an isoamyl group or hydrogen.

In Farmakol. i. Toksikol., pp 10–17 (1956), Liberman discloses a class of compounds having the general formula $(C_6H_5)_2CHCOSCH_2CH_2N$—$R_2$, wherein both R's are the same and are selected from methyl, ethyl, propyl and butyl groups; and a class of compounds having the general formula $(C_6H_5)$—$CH(C_6H_{11})COSCH_2CH_2N$—$R_2$, wherein both R's are the same and are selected from methyl, ethyl, propyl and butyl groups.

C. A. Buehler et al in the *Journal of Medicinal Chemistry*, 6, pp 230–3 (1963) disclose physiologically active compounds of the general formula $R(R')$—$C(OH)$-$COS(CH_2)_2NR''_2$ wherein R and R' are aryl groups.

R. O. Clinton et al in the *Journal of the American Chemical Society*, 68, pp 2076–7 (1946) synthesized a number of dialkyl aminoalkyl diarylthiolacetates including fluorene-9-carbothioic acid, S-[2-diethylaminoethyl]ester.

SUMMARY OF THE INVENTION

A new class of anti-spasmodic compounds is provided having the general formula:

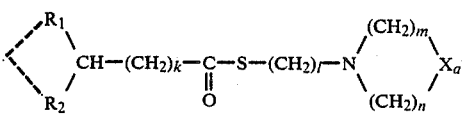

where $R_1$ and $R_2$ are saturated straight chain or branched alkyl groups containing from 1 to 8 carbon atoms, and are separate or linked to one another to form an aliphatic ring and k is an integer from 0 to 5, and the total number of carbon atoms in $R_1$ plus $R_2$ plus k are equal to or less than 12, and wherein a is 0 or 1;
l is an integer from 1 to 3;
m is an integer from 1 to 3;
n is an integer from 1 to 3; and Provided that when a is 1, X is selected from the group consisting of O, S, NH and $CH_2$ and m and n are integers from 1 to 3; and when a is 0 then X is nonexistent and m and n are integers from 0 to 3 and the terminal group in both the n-chain and the m-chain is a methyl group; or pharmaceutically acceptable salts thereof.

Accordingly, this means that when X is nonexistent both m and n can be integers from zero to three and the terminal group in the m-chain and the n-chain can be methyl, ethyl, propyl or butyl.

A preferred sub-genus of the compounds having the above described general formula comprises the class of compounds wherein $R_1$ and $R_2$ are separate, straight chain alkyl groups containing from 1–4 carbon atoms and X is nonexistent.

The present invention also comprises methods of administering the above-described compounds for but not limited to the treatment of patients suffering from smooth muscle spasm such as pylorospasm in the upper and lower gastrointestinal tract, spasm associated with the gall bladder and common bile duct, as well as diarrhea, the irritable bowel syndrome, ureterospasm and bladder irritation, asthma and emphysema.

DESCRIPTION OF THE PREFERRED EMBODIMENTS

The anit-spasmodic compounds of the present invention are effective in a dosage range of from about 1 to about 15 mg/kilogram of body weight per day. A preferred dosage is in the range of from about 1.5 to about 11.5 mg/kilogram of body weight per day. A still more preferred dosage range is from about 3 to about 6 mg/kilogram of body weight per day.

The anti-spasmodic compounds of the present invention may be combined with a pharmaceutically acceptable carrier and can be administered orally, typically in tablets of 400 mg active ingredient, total 1155 mg, or by intravenous injection or by topical application.

Because the anti-spasmodic compounds of the present invention generally hydrolyze slowly in water, they are preferably not used as a serum or suspension unless used as a freshly prepared solution. It is possible, however, to encapsulate microspheres of these compounds in the form of a liquid suspension for administration to patients.

As specific examples of the compounds of the present invention, there can be mentioned:

2-ethyl-butyryl-thio-S-(2-diethylaminoethyl)ester.HCl  $(CH_3CH_2)_2$—CH—CO—S—$CH_2$—$CH_2$—N—$(CH_2CH_3)_2$.HCl 2-propyl-pentanoyl-thio-S-(2-diethylaminoethyl)-ester.HCl $(CH_3CH_2CH_2)_2$—CH—CO—S—$CH_2CH_2$—N—$(CH_2CH_3)_2$.HCl 6-cyclopentyl-hexanoyl-thio-S-(2-diethylaminoethyl)-ester.HCl

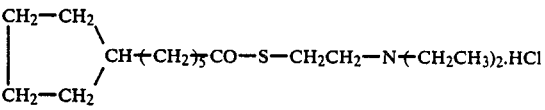

4-cyclopropyl-butyryl-thio-S-(2-diethylaminoethyl)-ester.HCl

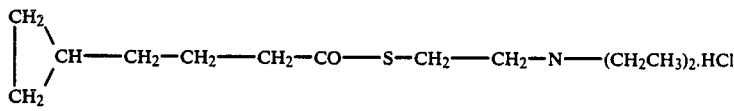

2-ethyl-butyryl-thio-S-(2-diethylaminoethyl)-ester.HCl

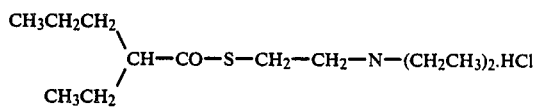

3-methyl-hexanoyl-thio-S-(2-morpholinoethyl)-ester

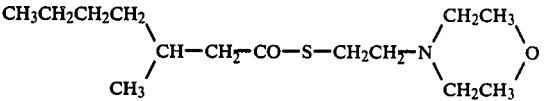

dibutyl acetyl-thio-S-(2-diethylaminoethyl)-ester.HCl
$(CH_3CH_2CH_2CH_2)_2$—CH—CO—S—$CH_2CH_2$—N—$(CH_2CH_3)_2$.HCl 4-ethyl-hexanoyl-thio-S-(2-diethylaminoethyl)-ester.HCl   $(CH_3CH_2)_2$CH—$CH_2$—$CH_2$—CO—S—$CH_2CH_2$—N—$(CH_2CH_3)_2$.HCl 3-cyclohexyl-propanoyl-thio-S-(2-diethylaminoethyl)-ester.HCl

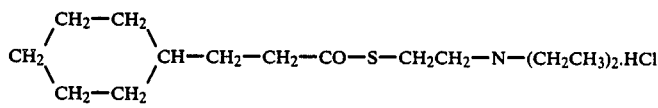

The general reaction used in the synthesis of the antispasmodic compounds described in the following examples of the present invention involves the nucleophilic substitution of certain acyl chlorides with certain thiol compounds, such as 2-diethylaminoethanethiol. This reaction is illustrated in the following formula, wherein Z represents as defined above:

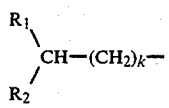

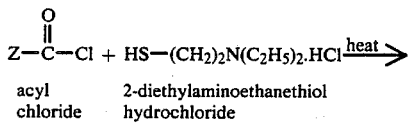

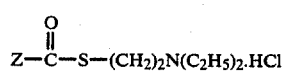

thiol ester hydrochloride 2-diethylaminoethanethiol was purified by re-distillation in vaccuo and nitrogen gas. Subsequently, the thiol was reacted with various acyl chlorides in dichloromethane by combining the two reactants in a 1:1 molar ratio and gently heating under reflux condensation for approximately 1-2 hours. The reaction mixture was then cooled in ice-water until crystallization occurred or, if necessary, in dry ice-ethanol. The crude crystals were harvested by suction filtration and were then recrystallized from an appropriate solvent (e.g. ethyl acetate, acetone, petroleum ether, or dichloromethane).

The desired acyl chlorides may be prepared from the carboxylic acid analogues by reaction with oxalyl chloride as follows:

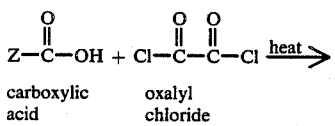

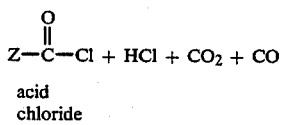

The reaction was performed under reflux condensation. Following the reaction, which was usually complete within a few hours, the acid chlorides were vacuum-distilled and reacted with a thiol compound as described above.

The compounds of this invention are anti-muscarinic agents (cholinergic-muscarinic receptor antagonists) which inhibit the actions of acetylcholine on autonomic effectors innervated by postganglionic cholinergic nerves as well as on smooth muscle that lacks cholinergic innervation. Since a major component of parasympathetic control of smooth muscle occurs via muscarinic receptors, these compounds are effective as modifiers of smooth muscle activity.

Thiphenamil hydrochloride has been shown to decrease spasm of the gastrointestinal tract, biliary tract, ureter and uterus without producing characteristic atropinic side effects on salivary and sweat glands, GI glands, the eye or the cardiovascular system. This invention results in compounds which are as efficacious as thiphenamil hydrochloride, or more so, in relaxing various smooth muscle systems while at the same time demonstrating thiphenamil hydrochloride's lack of associated side-effects. Pharmacological confirmation of these agents included in vitro organ bath work and development of actual receptor-binding data.

EXAMPLES 1 AND 2

The compounds of this invention were tested using a muscarinic receptor preparation from rabbit lung tissue. A measure of the ability of a particular compound to interact with muscarinic receptors, in this preparation, was determined by the degree to which a particular compound competed with [$^3$H] Quinuclidinyl Benzilate (hereinafter referred to as [$^3$H]QNB) for muscarinic receptors and thereby inhibited the usual tissue uptake of [$^3$H]QNB. Fresh peripheral lung tissue from New Zealand White rabbits was minced with scissors and homogenized with a polytron in 10 volumes of ice cold 50 mM sodium phosphate buffer (pH 7.4). The homogenate was centrifuged (1000×g, 5 min) and the supernatant collected. The supernatant was then centrifuged (42,000×g, 10 min, 4° C.) and the pellet resuspended in buffer. Following a final centrifugation (42,000×g, 10 min, 4° C.) the resulting pellet was resuspended in 2 ml of phosphate buffer for use in binding assays.

The [$^3$H]QNB binding assay was performed by incubating aliquots of the lung homogenates (0.8 mg protein/assay) at 37° C. for 60 min in 2 ml of sodium phosphate buffer which contained 0.1 nM [$^3$H]QNB in the presence of $1 \times 10^{-5}$M concentration of the anti-spasmodic compounds to determine inhibition of [$^3$H]QNB binding. Following incubation, the assay was terminated by the addition of ice-cold buffer and rapid filtration through Whatman GF-C glass fiber filters under suction in a Brandel cell harvester. The filters were removed, placed individually in 8 ml of scintillation cocktail, and counted for radioactivity in a scintillation spectrometer. [$^3$H]QNB which bound in the presence of 1 μM atropine was termed "nonspecific" and was substracted from that which bound in the absence of atropine (e.g. "specific" binding). All points were determined in duplicate.

| Compound/ formula | Molecular Weight (grams) | Melting Point (°C.) | % inhibition of $^3$H[QNB] binding (at a concentration of $1.0 \times 10^{-5}$ M) |
| --- | --- | --- | --- |
| 2-propyl-pentanoyl-thiol-S—(2-diethylaminoethyl)-ester. (CH$_3$CH$_2$CH$_2$)$_2$—CH—CO—S—(CH$_2$)$_2$—N—(CH$_2$CH$_3$)$_2$.HCl | 295.9 | 83 | 95% |
| 2-ethyl-butyroyl-thio-S—(2-diethylaminoethyl)-ester. (CH$_3$CH$_2$)$_2$—CH—CO—S— | 267.9 | 112 | 64% |

| Compound/formula | Molecular Weight (grams) | Melting Point (°C.) | % inhibition of $^3$H[QNB] binding (at a concentration of $1.0 \times 10^{-5}$ M) |
|---|---|---|---|
| $(CH_2)_2$—N—$(CH_2CH_3)_2$.HCl | | | |

EXAMPLE 3

The pharmacological actions of two anti-spasmodic compounds were studied in a rabbit urinary bladder strip preparation. In general, longitudinal strips were prepared from the base of freshly isolated rabbit bladders and were then suspended under near-physiological conditions in tissue baths. The strips were attached to force transducers and both contractile and relaxant activity was measured. To measure the relaxant effects on the anti-spasmodic compounds on previously-contracted bladder strips, the strips were initially exposed to the muscarinic receptor agonist bethanechol and allowed to reach a steady level of contractile activity for 20 minutes. At this point cumulative dose-responses to the various compounds were recorded. The rabbit abdomens were opened through a vertical midline incision. The bladder and urethra were dissected free of all surrounding tissues, removed and placed in aerated (95% $O_2$:5% $CO_2$) Kreb's-bicarbonate buffer (pH: 7.4) of the following composition (milliosmoles/liter): KCl 4.6, $CaCl_2.2H_2O$ 2.5, $KH_2PO_4$ 1.2, $MgSO_4.7H_2O$ 1.2, NaCl 118.2, $NaHCO_3$ 24.8, and glucose 10.0. Longitudinal muscle strips were prepared from the bladder base (approximately 6 mm×4 mm) and suspended in an organ bath containing Kreb's buffer (37° C.) which was continuously aerated with $O_2$:$CO_2$ (95%:5%). Tissues were allowed to equilibrate to a tension of 2 gm for sixty minutes during which time buffer was replaced at 20 minute intervals. The contractile and relaxant responses of the muscle strips were measured isometrically with a Statham UC3 force-displacement transducer and recorded on an Electronics for Medicine DR8 oscillographic recorder. Bethanechol was employed as the representative cholinergic agonist and, following equilibration, was added to the baths for a final concentration of 250 μM. The tissues were allowed 20 minute to achieve a maintained level of contraction in response to bethanechol and, at this point, cumulative dose-response measurements for two anti-spasmodic compounds were started at concentrations ranging from $10^{-8}$M to $10^{-4}$M. Solutions were added in volumes up to 100 μl and were prepared fresh each day by dissolving them in distilled: deionzed water. Responses were measured 5 minutes following any particular cumulative addition and were expressed as a percentage of maximal relaxation (e.g. maximal relaxation is the baseline or pre-bethanechol level of muscle tone).

Dose responses, measured from the standard bethanechol-contracted rabbit bladder strips, at various concentrations of 2-ethyl-butyrol-thio-S-(2-diethylaminoethyl)-ester [$CH_3CH_2)_2$—CH—CO—S—$(CH_2)_2$—N—$(CH_2CH_3)_2$.HCl], are presented in Table I:

TABLE I

| | Concentration (moles/liter) | | | | |
|---|---|---|---|---|---|
| | $10^{-8}$ | $10^{-7}$ | $10^{-6}$ | $10^{-5}$ | $10^{-4}$ |
| Increase in length of rabbit bladder strip (cm) | 0.3 | 0.4 | 0.6 | 0.7 | 1.3 |
| Decrease in force of contraction of rabbit bladder strip (gm) | 0.13 | 0.17 | 0.25 | 0.29 | 0.54 |
| % of maximum relaxation | 8.6 | 11.4 | 17.1 | 20.0 | 37.0 |
| % background relaxation | 4.6 | 4.6 | 5.4 | 5.4 | 17.5 |

EXAMPLE 4

Dose responses, measured from the standard bethanechol-contracted rabbit bladder strips, at various concentrations of 2-propyl-pentanoyl-thiol-S-(2-diethylaminoethyl)-ester.HCl [$(CH_3CH_2CH_2)_2$—CH—CO—S—$(CH_2)_2$—N—$(CH_2CH_3)_2$.HCl] are presented in Table II:

TABLE II

| | Concentration (moles/liter) | | | | |
|---|---|---|---|---|---|
| | $10^{-8}$ | $10^{-7}$ | $10^{-6}$ | $10^{-5}$ | $10^{-4}$ |
| Increase in length of rabbit bladder strip (cm) | 0.0 | 0.0 | 0.0 | 1.1 | 2.9 |
| Decrease in force of contraction of rabbit bladder strip (gm) | 0.0 | 0.0 | 0.0 | 0.31 | 0.81 |
| % of maximum relaxation | 0.0 | 0.0 | 0.0 | 100 | 100 |
| % background relaxation | 0.0 | 0.0 | 0.0 | 55 | 100 |

The following is claimed:

1. An antispasmodic compound of the formula

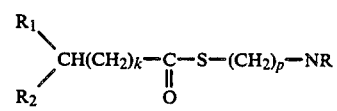

wherein $R_1$ and $R_2$ are saturated straight chain or branched alkyl groups from one to eight carbon atoms, and are independent alkyl groups not interconnected and k is an integer from zero to five, and the total number of carbon atoms in $R_1$ and $R_2$ plus k are equal to or less than twelve, and wherein p is an integer from one to three; NR is selected from the group consisting of pyrrolidino, piperidino, morpholino and dialkylamino containing a total of two to eight carbon atoms either straight chain or branched; or pharmaceutically acceptable salts thereof.

2. An antispasmodic compound as defined in claim 1, wherein $R_1$ and $R_2$ are separate, saturated chain alkyl group having one to four carbon atoms.

3. The compound as defined in claims 1 or 2, wherein $R_1$ is a propyl group, $R_2$ is an ethyl group, p=2 and k=zero.

4. The compound as defined in claim 1 or 2, wherein both $R_1$ and $R_2$ are butyl groups, p=2 and k=zero.

5. The compound as defined in claim 1, wherein $R_1$ is a butyl group, $R_2$ is a methyl group, p=2, k=one and NR is morpholino.

6. The compound as defined in claim 1 or 2, wherein both $R_1$ and $R_2$ are ethyl groups, $p=2$, and, $k=2$.

7. The compound as defined in claim 1 or 2, wherein both $R_1$ and $R_2$ are propyl groups; $p=2$, and $k=$ zero.

8. The compound as defined in claim 1 or 2, wherein both $R_1$ and $R_2$ are ethyl groups, $p=2$, and $k=$ zero.

9. A method of treating a patient suffering smooth muscle spasm comprising administering to the patient a therapeutically effective amount of a compound having the formula

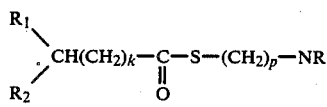

wherein $R_1$ and $R_2$ are saturated straight chain or branched alkyl groups from one to eight carbon atoms, and are independent alkyl groups not interconnected and k is an integer from zero to five, and the total number of carbon atoms in $R_1$, and $R_2$ plus k are equal to or less than twelve, and wherein p is an integer from one to three;

NR is selected from the group consisting of pyrrolidino, piperidino, morpholino and dialkylamino containing a total of two to eight carbon atoms either straight chain or branched; or pharmaceutically acceptable salts thereof.

10. A method of treating a patient suffering smooth muscle spasm comprising administering to the patient a therapeutically effective amount of a compound having the formula

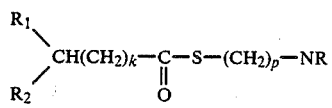

wherein $R_1$ and $R_2$ are separate, saturated straight chain alkyl groups containing from one to four carbon atoms, k is an integer from zero to five and the total number of carbon atoms in $R_1$ plus $R_2$ plus k are equal to or less than 12, and wherein p is an integer from one to three; and NR is selected from the group consisting of pyrrolidino, piperidino, morpholino and dialkylamino containing a total of two to eight carbon atoms either straight chain or branched.

11. The method as defined in claim 9 or 10, wherein the compound is administered in a dosage of from about one to about fifteen mg/kg of body weight per day.

12. The method as defined in claim 9 or 10, wherein the compound is administered in a dosage of from about 1.5 to about 11.5 mg/kg of body weight per day.

13. The method as defined in claim 9 or 10 wherein the compound is administered in a dosage of from about 3 to about 6 mg/kg of body weight per day.

14. The method as defined in claim 9 or 10, wherein the compound is combined with a pharmaceutically acceptable carrier.

* * * * *